US011771785B2

(12) United States Patent
Bassiri et al.

(10) Patent No.: US 11,771,785 B2
(45) Date of Patent: Oct. 3, 2023

(54) UNTETHERED DISENFECTING STETHOSCOPE SYSTEM

(71) Applicant: Bassiri, Inc., Tustin, CA (US)

(72) Inventors: Daryoush Bassiri, Tustin, CA (US); Phil Martie, Long Beach, CA (US)

( * ) Notice: Subject to any disclaimer, the term of this patent is extended or adjusted under 35 U.S.C. 154(b) by 510 days.

(21) Appl. No.: 16/872,151

(22) Filed: May 11, 2020

(65) Prior Publication Data

US 2020/0353116 A1 Nov. 12, 2020

Related U.S. Application Data

(60) Provisional application No. 62/846,094, filed on May 10, 2019.

(51) Int. Cl.
| | |
|---|---|
| *A61L 2/24* | (2006.01) |
| *A61L 2/10* | (2006.01) |
| *H04L 9/40* | (2022.01) |
| *G16H 40/40* | (2018.01) |
| *G16H 40/20* | (2018.01) |

(Continued)

(52) U.S. Cl.
CPC ............... *A61L 2/24* (2013.01); *A61B 7/02* (2013.01); *A61L 2/10* (2013.01); *G16H 40/20* (2018.01); *G16H 40/40* (2018.01); *G16H 40/67* (2018.01); *H04L 63/0428* (2013.01); *A61B 90/98* (2016.02); *A61L 2202/11* (2013.01); *A61L 2202/121* (2013.01); *A61L 2202/122* (2013.01); *A61L 2202/14* (2013.01); *A61L 2202/16* (2013.01); *A61L 2202/24* (2013.01); *G06F 1/1632* (2013.01); *G06F 21/6263* (2013.01)

(58) Field of Classification Search
CPC .......... A61L 2/24; A61L 2/10; A61L 2202/11; A61L 2202/121; A61L 2202/122; A61L 2202/14; A61L 2202/16; A61L 2202/24; A61B 7/02; A61B 90/98; G16H 40/20; G16H 40/40; G16H 40/67; H04L 63/0428; G06F 1/1632; G06F 21/6263
See application file for complete search history.

(56) References Cited

U.S. PATENT DOCUMENTS

| | | | |
|---|---|---|---|
| 5,027,825 A * | 7/1991 | Phelps, Sr. ............... | A61B 7/04 600/528 |
| 6,490,351 B1 * | 12/2002 | Roberts ..................... | A61L 2/10 379/439 |

(Continued)

FOREIGN PATENT DOCUMENTS

WO    WO-02076513 A1 * 10/2002    ............... A61L 2/10

*Primary Examiner* — Regina M Yoo

(57) ABSTRACT

A system for sterilizing and wireless tethering of a stethoscope includes a portable electronic device configured to be coupled to a stethoscope and having a wireless transmitter configured to transmit a signal. The system further includes an enclosure defining a cavity for housing the stethoscope. The enclosure includes at least one light source configured to emit light at a wavelength designed to damage or destroy microbes. The enclosure further includes a wireless receiver configured to receive the signal transmitted by the wireless transmitter of the portable electronic device. The enclosure further includes a controller coupled to the wireless receiver and configured to determine a notification event in response to the portable electronic device being further from the enclosure than a predetermined distance based on the signal received by the wireless receiver.

19 Claims, 8 Drawing Sheets

(51) Int. Cl.
*G16H 40/67* (2018.01)
*A61B 7/02* (2006.01)
*G06F 21/62* (2013.01)
*A61B 90/98* (2016.01)
*G06F 1/16* (2006.01)

(56) References Cited

U.S. PATENT DOCUMENTS

| | | | | |
|---|---|---|---|---|
| 8,754,385 | B1* | 6/2014 | Gutman | B32B 1/06 |
| | | | | 250/455.11 |
| 9,107,973 | B1* | 8/2015 | Robinson | A61L 2/10 |
| 10,639,389 | B2* | 5/2020 | Paul | A61L 2/10 |
| 2002/0146343 | A1* | 10/2002 | Jenkins | A61L 2/10 |
| | | | | 422/24 |
| 2012/0051969 | A1* | 3/2012 | Nahman | A61B 7/02 |
| | | | | 422/28 |
| 2013/0078142 | A1* | 3/2013 | Gordon | A61L 2/10 |
| | | | | 220/660 |
| 2013/0183749 | A1* | 7/2013 | Aamodt | A61L 2/22 |
| | | | | 435/287.1 |
| 2013/0277574 | A1* | 10/2013 | Dayton | A61L 2/10 |
| | | | | 250/455.11 |
| 2016/0324996 | A1* | 11/2016 | Bilenko | A61L 2/24 |
| 2017/0224858 | A1* | 8/2017 | Stibich | A61L 2/26 |
| 2017/0348452 | A1* | 12/2017 | Kuzelka | A61B 90/98 |
| 2018/0147023 | A1* | 5/2018 | Van Den Houdt | A61L 2/183 |
| 2019/0117809 | A1* | 4/2019 | Katz | G06T 7/50 |
| 2022/0047745 | A1* | 2/2022 | Neveu | A61B 90/96 |

* cited by examiner

UNTETHERED DISENFECTING STETHOSCOPE SYSTEM

CROSS-REFERENCE TO RELATED APPLICATIONS

This application claims the benefit and priority of U.S. Provisional Patent Application No. 62/846,094, titled "Untethered Disenfecting Stethoscope System" and filed on May 10, 2019, the entire contents of which being hereby incorporated by reference herein.

BACKGROUND

1. Field

The present disclosure is directed to systems and methods for sterilizing and wireless tethering of a stethoscope, and for recording the sterilization and tethering data.

2. Background

Today, stethoscope use in hospitals is restrictive, unsanitary, and prone to loss. Medical professionals often fail to sterilize stethoscopes between uses, thus opening the door to potentially transferring microbes between patients or re-infecting patients who have overcome disease caused by microbes. Additionally, medical professionals often walk away from a patient room without leaving the stethoscope behind, leading to unintended loss of expensive stethoscopes. Some medical centers have tried to overcome this issue by physically tethering stethoscopes to a location by a patient bed. However, this tethering restricts the use of the stethoscope to a specific area within a patient room and may be uncomfortable for the medical professionals to use due to the restriction of space in which the stethoscope can be used.

Thus, there is a need in the art for systems and methods for sterilization of stethoscopes and for less restrictive tethering of stethoscopes.

SUMMARY

Disclosed herein is a system for sterilizing and wireless tethering of a stethoscope. The system includes a portable electronic device configured to be coupled to a stethoscope and having a wireless transmitter configured to transmit a signal. The system further includes an enclosure defining a cavity for housing the stethoscope. The enclosure includes at least one light source configured to emit light at a wavelength designed to damage or destroy microbes. The enclosure further includes a wireless receiver configured to receive the signal transmitted by the wireless transmitter of the portable electronic device. The enclosure further includes a controller coupled to the wireless receiver and configured to determine a notification event in response to the portable electronic device being further from the enclosure than a predetermined distance based on the signal received by the wireless receiver.

Also disclosed is a system for sterilizing and wireless tethering of a stethoscope. The system includes a portable electronic device configured to be coupled to a stethoscope and having a wireless transmitter configured to transmit a signal. The system further includes an enclosure defining a cavity for housing the stethoscope. The enclosure includes a door configured to configured to close in order to fully enclose the stethoscope within the enclosure. The enclosure further includes a sensor configured to detect a door close event in response to the door being closed. The enclosure further includes at least one light source configured to emit light at a wavelength designed to damage or destroy microbes. The enclosure further includes a wireless receiver configured to receive the signal transmitted by the wireless transmitter of the portable electronic device. The enclosure further includes a controller coupled to the wireless receiver. The controller is designed to determine a notification event in response to the portable electronic device being further from the enclosure than a predetermined distance based on the signal received by the wireless receiver. The controller is further designed to determine the door close event based on data detected by the sensor. The controller is further designed to control the light source to emit the light in response to determining the door close event.

Also disclosed is a method for sterilizing and wireless tethering of a stethoscope. The method includes transmitting, by a wireless transmitter of a portable electronic device configured to be attached to a stethoscope, a signal. The method further includes receiving, by a wireless receiver of an enclosure, the signal. The method further includes determining, by a controller of the enclosure, a notification event in response to the portable electronic device being farther from the enclosure than a predetermined distance based on the signal received by the wireless receiver. The method further includes detecting, by a sensor, a door of the enclosure being closed. The method further includes controlling, by the controller, at least one light source of the enclosure to emit light at a wavelength designed to damage or destroy microbes in response to the door of the enclosure being closed.

BRIEF DESCRIPTION OF THE DRAWINGS

Other systems, methods, features, and advantages of the present disclosure will be or will become apparent to one of ordinary skill in the art upon examination of the following figures and detailed description. It is intended that all such additional systems, methods, features, and advantages be included within this description, be within the scope of the present disclosure, and be protected by the accompanying claims. Component parts shown in the drawings are not necessarily to scale, and may be exaggerated to better illustrate the important features of the present disclosure. In the drawings, like reference numerals designate like parts throughout the different views, wherein:

DETAILED DESCRIPTION

The present disclosure describes systems for automatically sterilizing and wirelessly tethering a stethoscope to a patient room. The systems provided in the present disclosure provide physicians with the potential to use a stethoscope that is reliably sterilized, findable, and provably linked to the same patient each and every time, and allows administrators and others to view records proving that the stethoscope was sterilized between each use. Achieving this goal will reduce the risk of infection, improve physician workflow, and improve patient and family confidence in the medical experience. Such record keeping of stethoscope sanitization and location also provides loss prevention benefits related to litigation by providing evidence against pathogen transmission between patients and reinfection of the same patient.

The system disclosed herein includes a wall-mountable container (i.e., an enclosure) located in each patient room or pod and assigned to a single patient, as well as a portable electronic device (such as a dongle) physically attached to a stethoscope. Use of the enclosure ensures that a stethoscope is reliably used on a 1-to-1 basis for each patient (i.e., each stethoscope is assigned to one patient), is provably sterilized in 100% of uses, that a stethoscope is always located in the right place, and that a stethoscope is easy to find.

Figure 1:
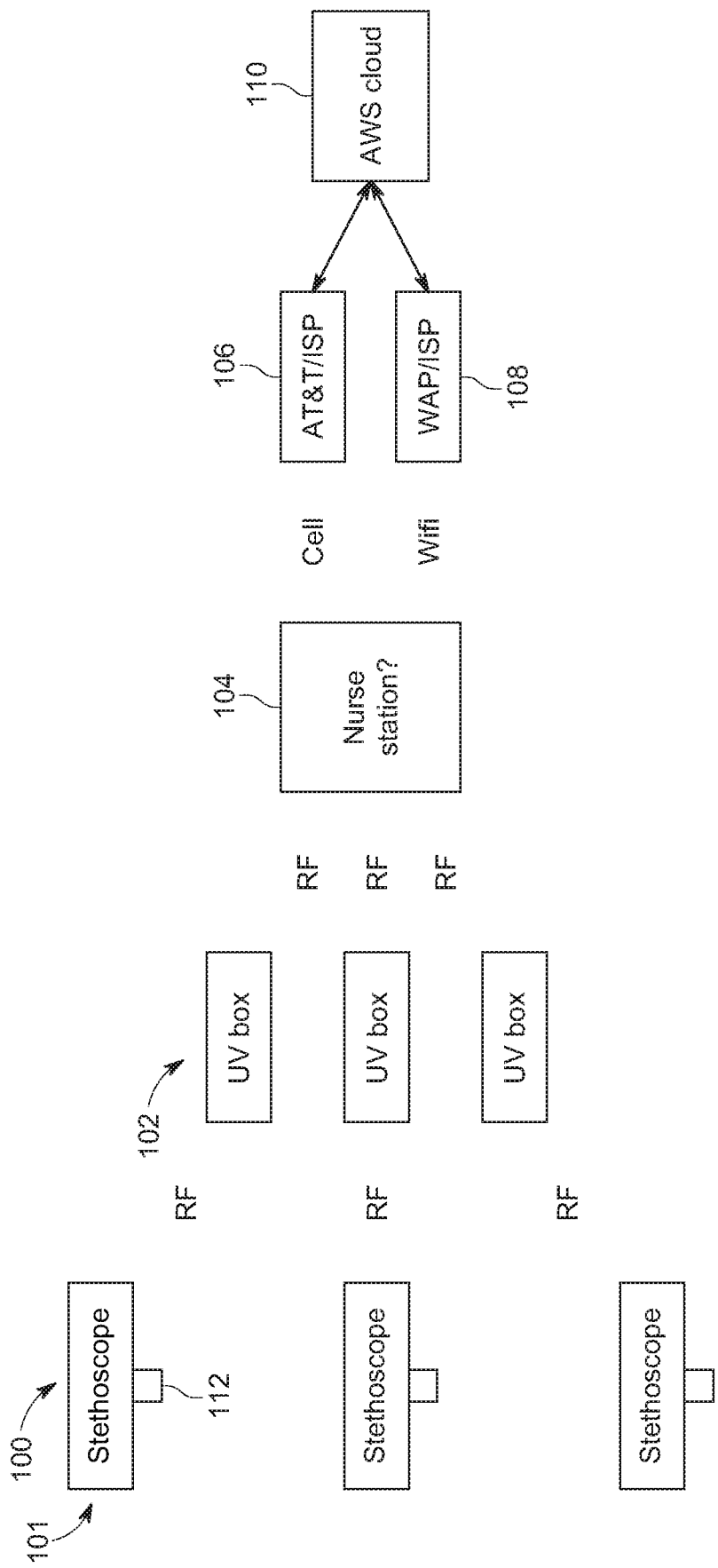
FIG. 1 is a block diagram illustrating a system for sterilizing and wireless tethering of stethoscopes, and for encrypting and storing the sterilization and tethering data, in accordance with various embodiments of the present disclosure.

Referring to FIG. 1, a system 101 for sterilizing and wireless tethering of a stethoscope is shown. The system 101 may include one or more stethoscope 100 and one or more enclosure 102. Each stethoscope 100 may be assigned to one enclosure 102, and each stethoscope/enclosure pair may be assigned to a single patient room or patient pod. Each enclosure 102 may be designed to sterilize its corresponding stethoscope 100 and may record data corresponding to a time or frequency of sterilization of the corresponding stethoscope 100. For example, the enclosure 102 may make record times of each sterilization.

Each stethoscope 100 may further include a portable electronic device 112, such as a dongle, connected thereto. The portable electronic device 112 may be permanently or removably attached to its corresponding stethoscope 100. In some embodiments, the portable electronic device 112 may communicate with an element of the stethoscope 100, such as an RFID tag, to ensure that the portable electronic device 112 is not removed from its associated stethoscope. The portable electronic device 112 of each stethoscope 100 may communicate with a corresponding enclosure 102, and the enclosure 102 may determine whether the corresponding stethoscope 100 has moved greater than or equal to a predetermined distance away from the corresponding enclosure based on the data received from the portable electronic device 112. In some embodiments, the portable electronic device 112 may record the data corresponding to the time or frequency of sterilization of each corresponding stethoscope 100 in addition to, or instead of, the enclosure 102 recording such data.

The system 101 may further include a data collection hub 104 (which may include a local database, a local server, or any other electronic storage or computing system). The data collection hub 104 may be located on site at the medical center and may communicate with at least one of the enclosures 102 or the portable electronic devices 112. In some embodiments, the portable electronic devices 112 may communicate directly with the hub 104 directly, may communicate with the hub 104 via the enclosure 102, or may fail to communicate with the hub 104. Similarly, the enclosure 102 may communicate directly with the hub 104, may communicate with the hub 104 via the portable electronic devices 112, or may fail to communicate with the hub 104.

The hub 104 may communicate via any wired or wireless protocol such as Wi-Fi, Bluetooth, Ethernet, a cellular protocol, or the like. The hub 104 may receive various information from at least one of the enclosures 102 or the portable electronic device 112 such as specific times at which a stethoscope 100 was sanitized, a frequency of sanitization of the stethoscope 100, a duration of sanitization of the stethoscope 100, times at which a stethoscope 100 was removed from the corresponding enclosure 102, a duration of each removal of the stethoscope 100 from the enclosure 102, a frequency of removal of the stethoscope 100 from the enclosure 102, whether the stethoscope 100 was transported away from the enclosure 102 by more than the predetermined distance (and a quantity of these events), average or actual distances from the enclosure 102 which the stethoscope 100 was moved, rooms or pods to which the stethoscope 100 is assigned, data relating to the use of the stethoscope 100 (e.g., how often it was used), an identifier of each patient to which the stethoscope 100 is assigned, or the like.

The hub 104 may store the received data in a local non-transitory memory, may transmit the received data to a cloud 110, or the like. For example, the hub 104 may communicate with the cloud 110 via a cellular protocol 106, a Wi-Fi protocol 108, or any other wired or wireless protocol. Inclusion of the hub 104 between the enclosures 102 and the cloud 110 allows for additional data security and privacy measures to be applied to the data before transmission over the internet. For example, the hub 104 may encrypt or otherwise protect the data prior to transmitting the data to the cloud 110. The encryption or other protection may be designed to comply with health insurance portability and accountability act (HIPAA) guidelines.

The cloud 110 may store the data in a non-transitory memory and may facilitate access to the data by authorized parties, such as via a direct connection to the cloud 110 or an internet connection to the cloud 110. Authorized users may include hospital administrators, investigators, healthcare watchdogs, or the like. Authorized users may be assigned a username and password and may access the data in the cloud 110 using the username and password. In some embodiments, the authorized user may be authorized to access the data in the cloud 110 using any authorization technique such as access by using an authorized device. The access of the data from the cloud 110 may also be performed in a secure way, such as encryption that complies with HIPAA guidelines.

Figure 2:
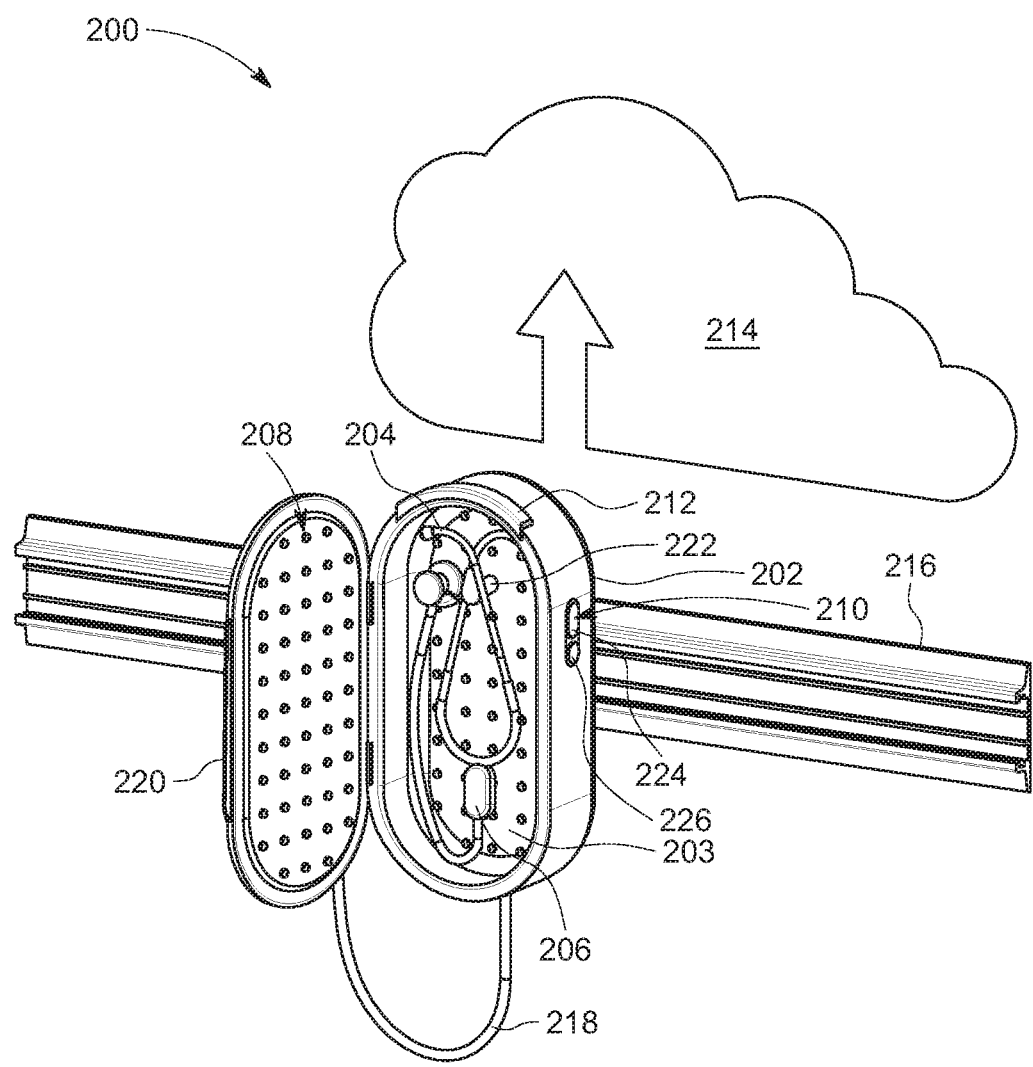
FIG. 2 is a perspective view of an enclosure for sterilizing and wireless tethering of a stethoscope with the stethoscope located in the enclosure, in accordance with various embodiments of the present disclosure.

Turning to FIG. 2, a system 200 for automatic sterilization and wireless tethering of a stethoscope is shown. The system 200 may include similar features as the system 101 of FIG. 1. The system 200 may include an enclosure 202, a stethoscope 204, and a portable electronic device 206 attached to the stethoscope 204. The portable electronic device 206 may be permanently or removably coupled to the stethoscope 204. For example, a leash or collar may be fastened to the portable electronic device 206 and may "snap" the portable electronic device 206 onto the stethoscope 204. As another example, an adhesive or a different fastener may attach the portable electronic device 206 onto the stethoscope 204. The portable electronic device 206 may be formed integrally with the stethoscope 204 or may be coupled to the stethoscope in a permanent manner (e.g., use of heavy-duty adhesive, fasteners, or the like) to reduce the likelihood of separation of the portable electronic device 206 from the stethoscope 204. In some embodiments, the portable electronic device 206 may include electronics that are fully integrated with the stethoscope such that the stethoscope 204 and the portable electronic device 206 are one in the same device.

The enclosure 202 may define a cavity 203 in which the stethoscope 204 may be stored and sanitized. In that regard, the enclosure 202 may include one or more light source 208 located within the cavity 203. The one or more light source 208 may include multiple light sources on none, some, or all interior surfaces of the enclosure 202 (i.e., all surfaces facing towards the cavity), on none, some, or all interior surfaces of a door 220, and on none, some, or all of any other components located in the cavity 203 such as a support hook 222. The light source 208 may include multiple relatively small light sources as shown in FIG. 2, may include elongated light sources, may include light emitting diodes (LEDs), halogen bulbs, or any other type of light source.

The one or more light source 208 may emit ultraviolet C light into the cavity 203 in order to sterilize the stethoscope 204. For example, the one or more light source 208 may emit light having a wavelength between 180 nanometers (nm) and 400 nm, between 220 nm and 280 nm, between 240 and 270 nm, or about 254 nm. Where used in this context, about refers to the reference to value plus or minus 5 percent (5%) of the reference value. Light in these wavelength ranges may provide optimal sterilization of the stethoscope.

The enclosure 202 may include sensors and logic devices that determine when the door 220 of the enclosure 202 is closed. In response to closure of the door 220, the logic device may control the light source 208 to emit the ultraviolet light. The logic device may control the light source 208 to emit the light for a predetermined amount of time, such as an amount of time sufficient to fully sterilize the stethoscope 204. For example, the light source 208 may emit the light for between 10 seconds and 5 minutes, between 30 seconds and 4 minutes, between 1 minute and 3 minutes, about 2 minutes, or the like.

The enclosure 202 may further include one or more input device 210 such as a button, knob, dial, or the like. The one or more input device 210 may include, for example, a start button, a stop button, a power button, or the like. The start button may be used to provide redundancy to the enclosure 202 (e.g., as a redundant input for controlling the light source 208 to emit the light), or to test operation of the light source 208. In response to selection of the start button, the logic device may control the light source 208 to emit the light for a predetermined amount of time. In response to selection of the stop button, the logic device may control the light source 208 to cease emitting the light. The power button may be depressed, or held in a depressed position for a predetermined amount of time, to provide or cease power to the enclosure 202. In various embodiments, the input device 210 may include a start button 224 and a power button 226.

The enclosure 202 may also include a status indicator 212 such as a speaker, a secondary light source, or the like. The status indicator 212 may indicate whether the stethoscope 204 is currently being sterilized, whether the stethoscope 204 is fully sterilized, whether the stethoscope 204 is located within a predetermined distance of the enclosure 202, whether the stethoscope 204 has been moved farther than the predetermined distance from the enclosure 202 (ever or since a last status check), or the like. In that regard, the portable electronic device 206 may include a transmitter designed to transmit a signal to a receiver of the enclosure 202. Based on the received signal, the logic device of the enclosure 202 may determine whether the portable electronic device 206, and thus the stethoscope 204, is located within the predetermined distance of the enclosure 202. In some embodiments, the portable electronic device 206 may determine whether the portable electronic device 206 (and thus the stethoscope 204) has been moved farther than the predetermined distance from the enclosure, either based on inertial measurement unit (IMU) data (e.g., from a gyroscope) or based on a received signal from the logic device of the enclosure 202. In such embodiments, the portable electronic device 206 may at least one of transmit a signal to the logic device of the enclosure 202 indicating the movement or transmit a signal directly to a hub (e.g., the hub 104 of FIG. 1).

In response to the stethoscope 204 being located farther than the predetermined distance from the enclosure 202, the logic device of the enclosure 202 may control the status indicator 212 to output a warning signal (e.g., by turning on a steady or flashing light, or by controlling a speaker to output an audio signal), may transmit a warning signal to a remote device (such as a mobile phone or a beeper associated with a medical professional), may transmit a warning signal to a central hub or the cloud 214, may transmit a warning signal to a device associated with hospital administrators, or the like.

In some embodiments, the status indicator 212 may output a warning if the stethoscope 204 is kept out of the enclosure 202 for at least a predetermined amount of time (indicating that the stethoscope 204 has not been sanitized properly), or the logic device may transmit a corresponding warning signal to a remote device. In some embodiments, a central location, such as a nurse station, may have an output device that outputs all warnings associated with stethoscopes assigned to the central location. For example, an intensive care unit (ICU) may have a single central location designed to output these warnings, and all stethoscopes in the ICU may report their status to the central location. In some embodiments, the enclosure 202 may further determine when the stethoscope is located within the enclosure 202 and may output a warning if the enclosure is closed without the stethoscope located therein.

As referenced above, the enclosure 202 may be designed to communicate with the cloud 214. In that regard, the enclosure 202 may include a network access device designed to transmit and receive signals, and the logic device of the enclosure 202 may communicate with the cloud 214 via the network access device. In some embodiments, one or both of the enclosure 202 or the portable electronic device 206 may communicate with a server (as discussed with reference to FIG. 1) which may then communicate with the cloud 214.

The enclosure 202 may further include a power source 218 such as a single use or rechargeable battery, a power cable or strip designed to be plugged into a wall socket or other external power source, or the like. The power received from the power source 218 may be used to power the light source 208, sensor or sensors, logic device, network access device, receiver, or the like. In some embodiments, the enclosure 202 may include a wireless charger designed to wirelessly transmit electrical energy to the portable electronic device 206. In that regard, the portable electronic device 206 may be wirelessly charged while stored in the enclosure 202. In some embodiments, the portable electronic device 206 may include a replaceable battery or a rechargeable battery in order to power the components of the portable electronic device 206.

In some embodiments, the enclosure 202 may be designed to be permanently or removably attached to a surface, such as a wall, or to a rail in a patient room or pod. In some embodiments, the enclosure 202 may include a permanent or removable stand. The stand may include any stand coupled to the enclosure 202 and capable of supporting the enclosure on a flat or other surface (e.g., a desk, floor, table, or the like).

Figure 3:
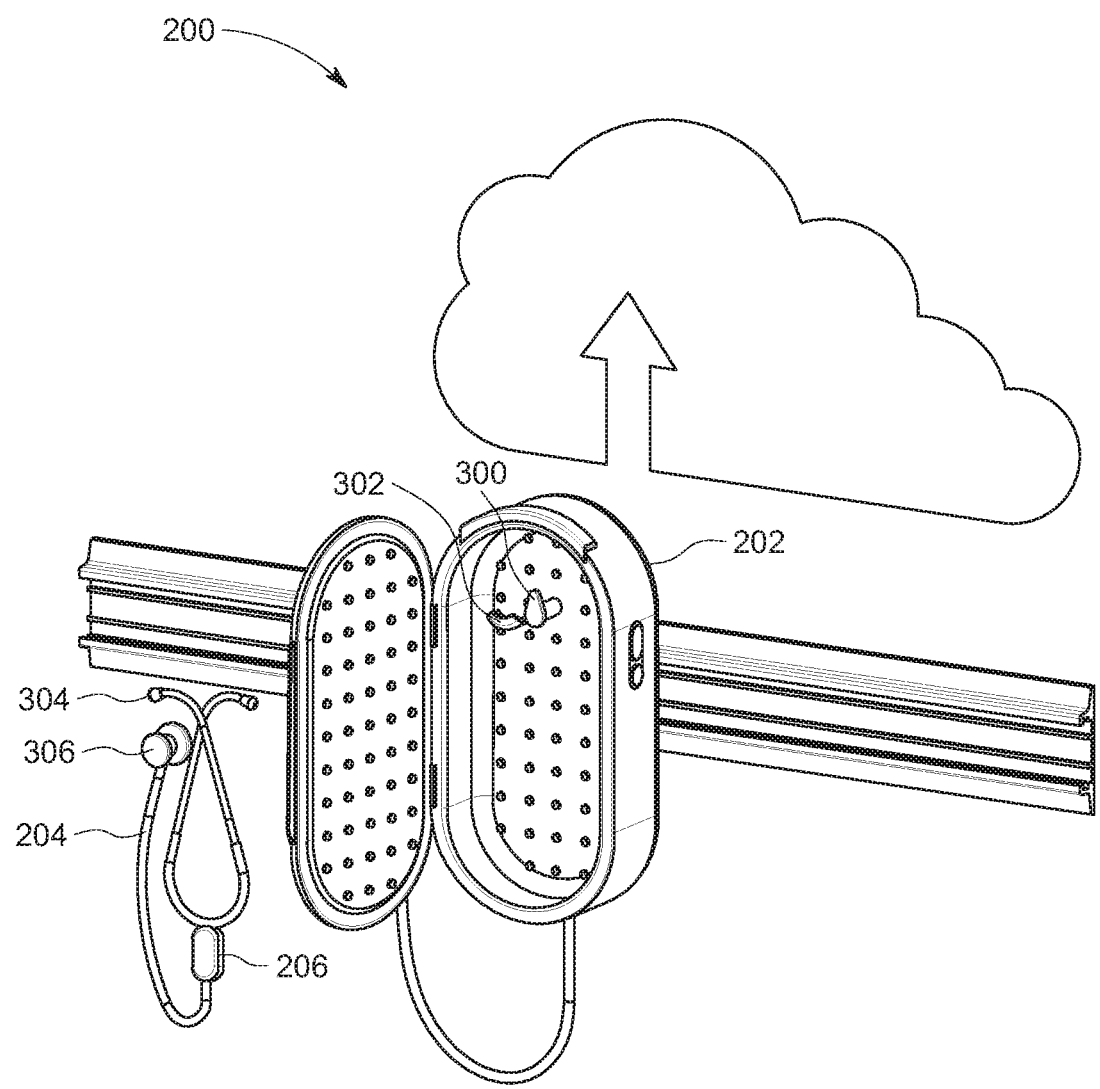
FIG. 3 is a perspective view of the enclosure of FIG. 2 with the stethoscope removed from the enclosure, in accordance with various embodiments of the present disclosure.

Referring now to FIG. 3, the enclosure 202 may further include a first hook 300 positioned adjacent to a second hook 302. As shown in FIGS. 2 and 3, the first hook 300 may be designed to receive and support the headset 304 of the stethoscope 204 at an intersection of the arms of the headset 304. The second hook 302 may be designed to receive and support the diaphragm 306 of the stethoscope 204. In response to the stethoscope 204 being positioned on the first hook 300 and the second hook 302, the stethoscope 204 may be fully supported in a lifted or raised position within the enclosure 202. The hooks 300, 302 illustrate one manner of supporting the stethoscope 204 within the enclosure 202. However, one skilled in the art will realize that the disclosure includes all means for supporting the stethoscope 204 in the enclosure in such a way as to allow all surface of the stethoscope 204 to be exposed to the emitted light.

Figure 4:
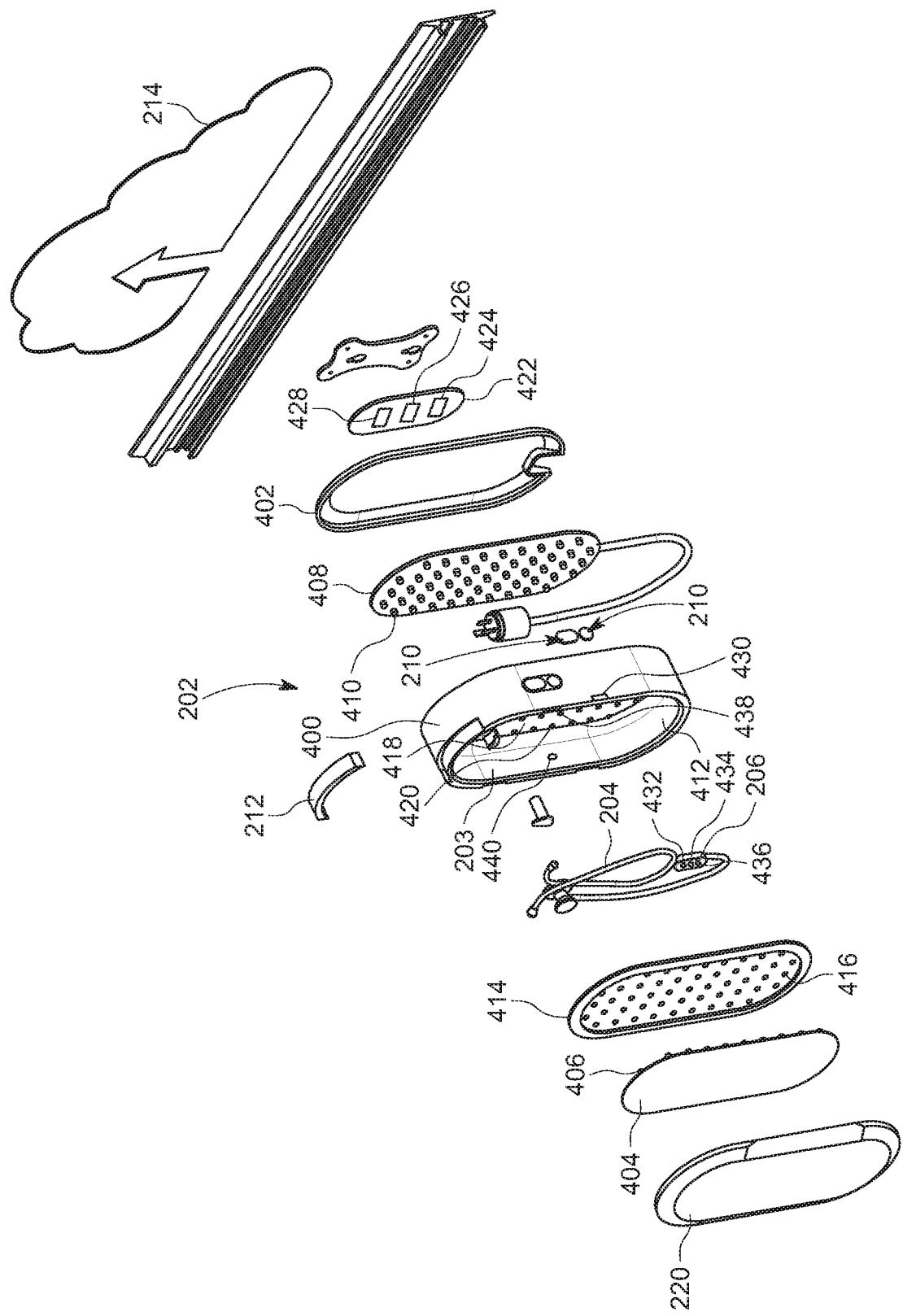
FIG. 4 is an enlarged view of the enclosure of FIG. 2 illustrating various components of the enclosure, in accordance with various embodiments of the present disclosure.

Turning to FIG. 4, an exploded view of the enclosure 202 illustrates additional features of the enclosure 202. In particular, the enclosure 202 may include an oval frame 400 that at least partially defines the cavity 203. The enclosure 202 may further include the door 220 which may likewise be oval in shape. The door 220 may be designed to be opened to allow access to the cavity 203, and to be closed to enclose a stethoscope within the cavity 203. In that regard, the door 220 may be coupled to the oval frame 400 via one or more hinge, and a latch may be used to fasten the door 220 to the oval frame 400 to prevent unwanted opening of the door 220.

The enclosure 202 may also include an oval back cover 402 which may further enclose the cavity 203. The enclosure 202 may also include a front board 404, such as a printed circuit board (PCB) which may include a first plurality of light emitting elements 406, such as LEDs. The front board 404 may be designed to be coupled to the door 220. The enclosure 202 may further include a back board 408 which may be similar to the front board 404 and may include a second plurality of light emitting elements 410. The backboard 408 may be designed to be coupled to the oval back cover 402. The first plurality of light emitting elements 406 and the second plurality of light emitting elements 410 may emit ultraviolet C light, as discussed above.

In some embodiments, an inner surface 412 of the oval frame 400 may include a reflective coating in order to reflect light emitted by the light emitting elements 406, 410. In some embodiments, the inner surface 412 may also include light emitting elements that emit ultraviolet C light. Additionally, the enclosure 202 may include a first reflective surface 414, such as a metallic or other sheet, which defines openings 416 each designed to receive one of the first plurality of light emitting elements 406. The enclosure 202 may also include a second reflective surface 418 which may include a metallic or other sheet and likewise defines openings 420 each designed to receive one of the second plurality of light emitting elements 410. In some embodiments, the first reflective surface 414 may be located between the door 220 and the cavity 203, and the second reflective surface 418 may be located between the oval back cover 402 and the cavity 203. In that regard, the reflective coating of the inner surface 412, the first reflective surface 414, and the second reflective surface 418 may each reflect light emitted by the first plurality of light emitting elements 406 and the second plurality of light emitting elements 410 in order to increase the amount (e.g., lumens) of light that reach each surface of a stethoscope within the cavity 203.

In some embodiments, the second reflective surface 418 may be built integral or monolithic with the oval frame 400, may be formed separately from the oval frame 400 and coupled to the oval frame 400, or the like. In response to assembly and closure of the enclosure 202, the light emitting elements 406, 410 may emit light which may be reflected by the reflected surfaces to ensure the entire surface of a received stethoscope is sanitized. Sanitization of all surfaces of the stethoscope is desirable as pathogens may exist on any surface of the stethoscope.

The enclosure 202 may also include a circuit board 422, such as a printed circuit board. The circuit board 422 may include a controller or processor 424, a network access device 426, and a receiver 428. The controller 424 may control operation of the light emitting elements 406, 410 based on data received from a sensor 430 corresponding to a state of the door 220 or based on data received from the input device 210. The controller 424 may also control operation of the status indicator 212 based on a determined status of the enclosure 202.

The receiver 428 may receive data from a transmitter 432 of the portable electronic device 206 associated with the stethoscope 204. For example, the receiver 428 and transmitter 432 may communicate via a wireless protocol such as near field communications (NFC), Bluetooth, Wi-Fi, optical signaling, or the like. In some embodiments, the receiver 428 and transmitter 432 may facilitate two-way communications, or communications may be one way from the transmitter 432 to the receiver 428. The data may correspond to a distance between the portable electronic device 206 and the enclosure 202. For example, the transmitter 432 may transmit an absolute location of the stethoscope (based on GPS or inertial measurement data from a location sensor 434), or the receiver 428 may determine the distance to the stethoscope 204 based on a signal strength of the received signal or based on other metrics. Based on the data received by the receiver 428, the controller 424 may determine a distance between the stethoscope 204 and the enclosure 202. As described above, the controller 424 may take an action in response to determining that the stethoscope 204 is greater than or equal to a predetermined distance away from the enclosure 202. This in effect provides a wireless tethering of a stethoscope to the enclosure 202.

In some embodiments, the portable electronic device 206 may likewise include a processor or controller 436. The controller 436 may receive sensor information from the location sensor 434, may determine the location based on the received information, may control operation of the transmitter 432, or the like. In some embodiments, the transmitter 432 may be a passive transmitter (e.g., near field communications) such that the receiver 428 provides a wireless power signal to the transmitter 432 and receives a signal in response to providing the wireless power signal.

The network access device 426 may communicate via one or more wired or wireless protocol such as ethernet, Wi-Fi, Bluetooth, or the like. The controller 424 may control the network access device 426 to transmit data to the cloud 214 such as a sterilization record, recorded distances between the stethoscope and the enclosure 202, or the like.

The controller 424 may likewise be coupled to a sensor 438 capable of detecting a status of the door 220 (e.g., a switch). For example, the sensor 438 detects whether the door 220 is in an open or closed state. In some embodiments, the enclosure 202 may further include a sensor 440 (e.g., a proximity sensor, a pressure sensor, a camera, or the like) that detects the presence of a stethoscope within the enclosure. The controller 424 may control the light sources 406, 410 to emit the light for a predetermined amount of time in response to the door 220 being closed. In some embodiments, the controller 424 may only control the light sources 406, 410 to emit the light in response to the door 220 being closed and the stethoscope being detected within the enclosure 202. The controller 424 may also control the light sources 406, 410 to cease emitting the light in response to the door 220 being opened in order to reduce the likelihood of harmful ultraviolet light reaching skin of a human. The controller 424 may also control the light sources 406, 410 to emit the light in response to input received by an input device 210.

Figure 5:
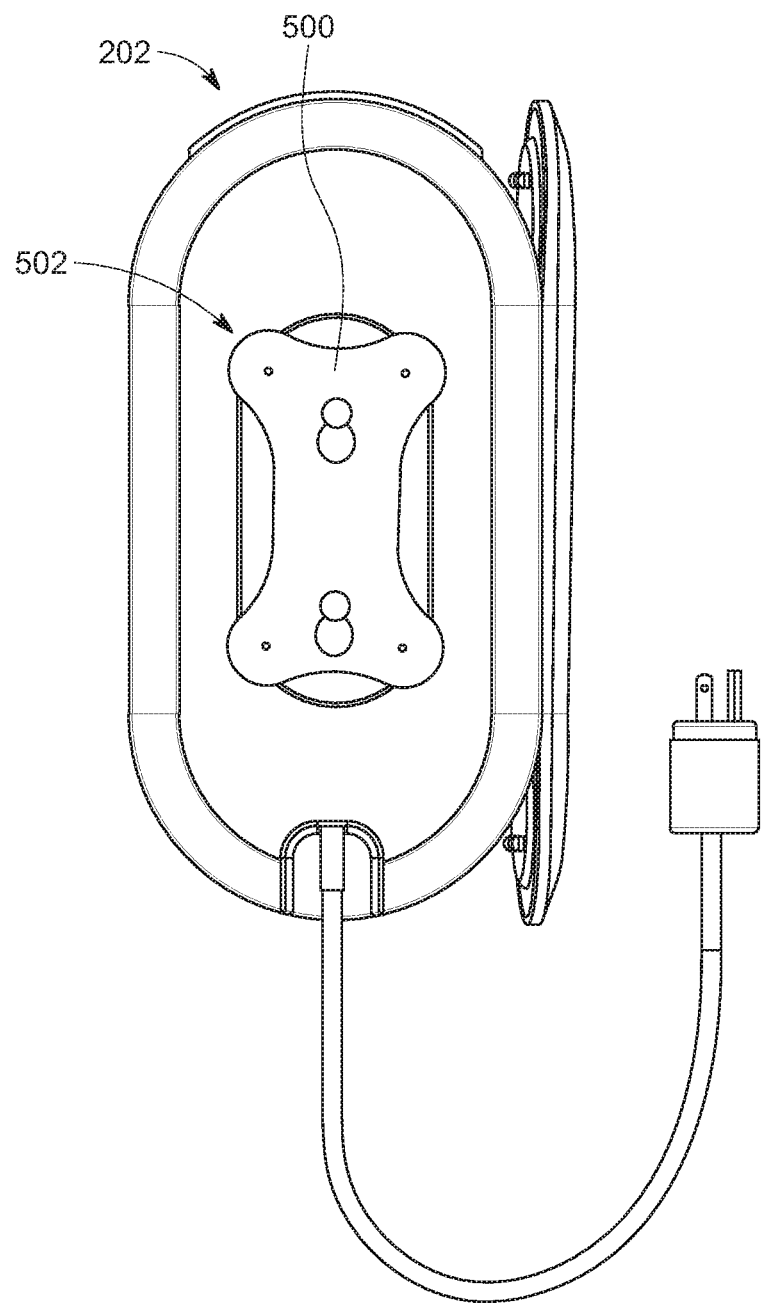
FIG. 5 is a rear view of the enclosure of FIG. 2, in accordance with various embodiments of the present disclosure.
Figure 6:
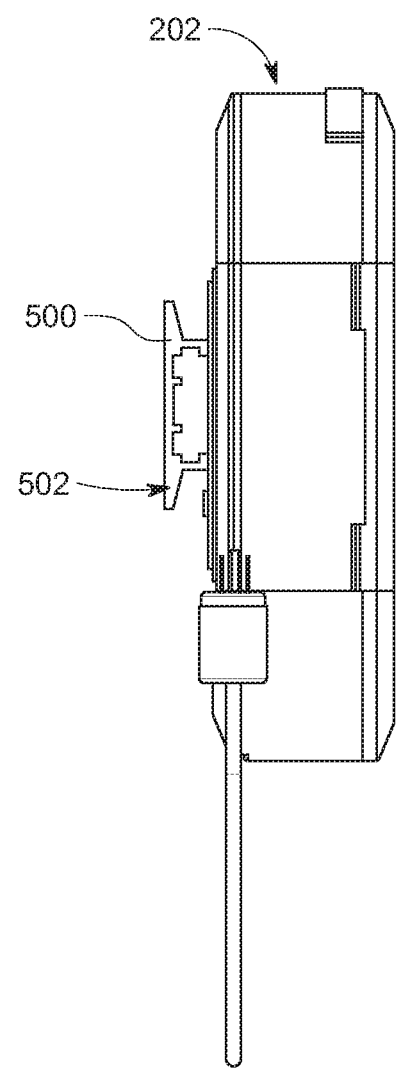
FIG. 6 is a profile view of the enclosure of FIG. 2, in accordance with various embodiments of the present disclosure.

Referring to FIGS. 2, 5, and 6, the enclosure 202 may include a connector 500 to attach the enclosure 202 to the rail 216. As shown, the connector 500 may include hooks or arms 502 usable to fasten the connector 500, and thus the enclosure 202, to the rail 216. The enclosure 202 may be coupled to the rail 216 in any other manner such as via fasteners, an adhesive, or the like. As referenced above, the enclosure 202 may include, or be coupled to, a stand that facilitates standing of the enclosure 202 on a flat surface.

Figure 7A:
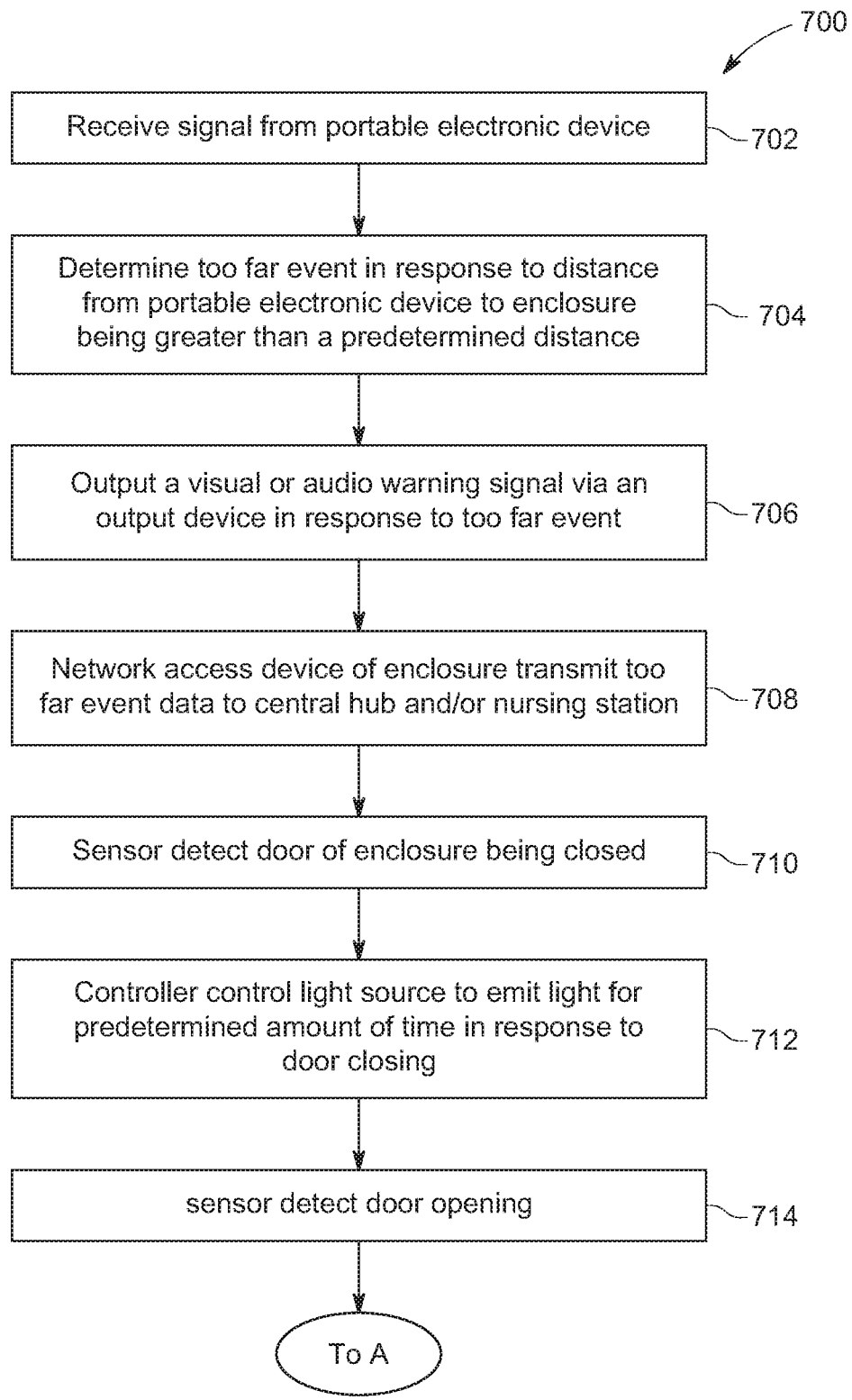
FIGS. 7A and 7B are flowcharts illustrating a method for sterilizing and wireless tethering of a stethoscope, in accordance with various embodiments of the present disclosure.
Figure 7B:
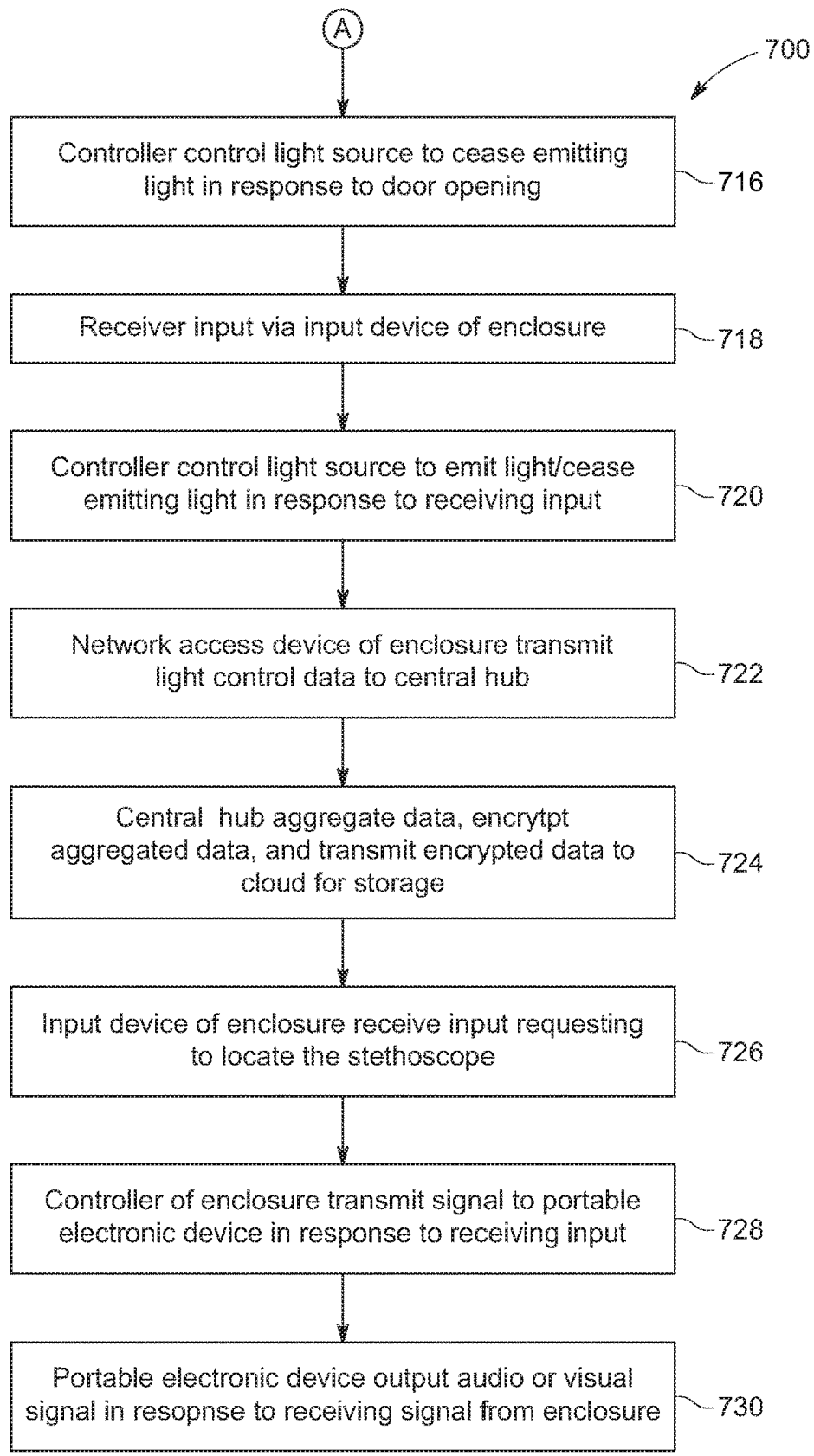

Referring to FIGS. 7A and 7B, a method 700 for sterilizing a stethoscope and for wireless tethering of the stethoscope is shown. The method 700 begins in block 702 where a receiver of an enclosure receives a signal from a portable electronic device attached to a stethoscope. The signal may include location data corresponding to a location of the portable electronic device or any other signal usable to determine a distance between the enclosure and the portable electronic device.

In block 704, a controller of the enclosure may determine a "too far" event in response to a distance between the portable electronic device and the enclosure being greater than a predetermined distance. In block 706, the enclosure may control an output device, such as an external light source or a speaker, to output a visual or audio warning signal in response to the controller determining the "too far" event. In some embodiments and in block 708, the controller may control a network access device of the enclosure to transmit data corresponding to the "too far" event to at least one of a central hub or a nurse station.

In block 710, a sensor the enclosure may detect a sensor door of the enclosure being closed. In some embodiments, the same sensor or another sensor may further detect whether the stethoscope is located within the enclosure. In block 712, the controller of the enclosure may control an internal light source of the enclosure to admit ultraviolet radiation for a predetermined amount of time in response to the door being closed (and, in some embodiments, in response to the stethoscope being located within the enclosure).

In block 714, a sensor the enclosure may detect the door opening. In block 716, the controller may control the light source to cease emitting the ultraviolet light in response to the door opening. This reduces the likelihood of harmful ultraviolet radiation reaching human skin.

In block 718, an input device of the enclosure may receive user input. For example, a user may depress a start button of the enclosure. In block 720, the controller may control the light source to emit the light or to cease emitting the light in response to receiving the input from the input device. For example, a first depression of the start button may cause the light source to emit the light (e.g., for a predetermined amount of time), and a second depression of the start button may cause the light source to cease admitting the light.

In some embodiments, the input of block 718 may be received from a remote device. For example, a nurse station may identify that the stethoscope has failed to be sanitized within an acceptable amount of time. An input device at the nurse station may be selected in order to control the enclosure to generate the ultraviolet light to sanitize the stethoscope. In some embodiments, the controller of the enclosure may determine that the stethoscope has failed to be sanitized within the acceptable amount of time and may itself control the light source to emit the light in response to this determination.

In block 722, the controller of the enclosure may control a network access device to transmit light control data to the central hub. The light control data may include times at which the light source generated the light, a duration of light generation, a frequency of light generation, the trigger for light generation (e.g., selection of the local input device, instructions from a nurse station, closure of the door) a frequency of use of the stethoscope, or any other information corresponding to light generation within the enclosure or use of the stethoscope or enclosure.

In block 724, the central hub may aggregate the received data (e.g., the location data, any generated warnings by the enclosure, the light data, or any other data detected or generated by the enclosure). The central hub may further encrypt the aggregated data. In some embodiments, the central hub may transmit the encrypted data to a cloud server for storage, in some embodiments the encrypted or original data may be stored locally at the central hub, or the like. Hospital administrators or other authorized users may access the data from the cloud server or the central hub.

In block 726, an input device of the enclosure may receive input corresponding to a request to locate the stethoscope. As with block 718, the input may also be received from a remote device, such as from a nurse station. In block 728, the controller of the enclosure may transmit a signal to the portable electronic device in response to receiving the input. In block 730, the portable electronic device may output audio or visual data that may alert the user to the location of the stethoscope. In some embodiments, the portable electronic device may transmit location data corresponding to the location of the portable electronic device to the enclosure, a nurse station, or the like. In response to receiving this location data, the enclosure or the nurse station may output the location data in a usable format, such as by displaying a map with the location of the portable electronic device on the map.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for sterilizing and wireless tethering of a stethoscope, the system comprising:
a portable electronic device configured to be coupled to a stethoscope and having a wireless transmitter configured to transmit a signal; and
an enclosure defining a cavity for housing the stethoscope and having:
a plurality of light emitting elements configured to emit light at a wavelength designed to damage or destroy microbes,
a wireless receiver configured to receive the signal transmitted by the wireless transmitter of the portable electronic device,
a controller coupled to the wireless receiver and configured to determine a notification event in response to the portable electronic device being further from the enclosure than a predetermined distance based on the signal received by the wireless receiver,
a frame at least partially defining the cavity,
a door configured to open to allow access to the cavity and to close to enclose the stethoscope within the cavity,
a back cover,
a front board having a first plurality of light emitting elements of the plurality of light emitting elements and configured to be coupled to the door,
a back board having a second plurality of light emitting elements of the plurality of light emitting elements and configured to be coupled to the back cover, and
a circuit board configured to support the controller.

2. The system of claim 1 wherein:
the enclosure further includes at least one of a speaker or a light source configured to emit an audible or visible notification, respectively; and
the controller is configured to control the at least one of the speaker or the light source to emit the audible or visible notification in response to determining the notification event.

3. The system of claim 1 wherein the controller is further configured to cause a notification to be transmitted to a remote device in response to determining the notification event.

4. The system of claim 1 wherein the controller is further configured to determine or store sterilization record data corresponding to at least one of a time or a frequency at which the plurality of light emitting elements emitted the light.

5. The system of claim 4 wherein the controller is further configured to cause the sterilization record data to be transmitted to a server.

6. The system of claim 5 wherein the server is configured to at least one of store a sterilization record including the sterilization record data transmitted by the controller or to transfer the sterilization record to a cloud server for storage.

7. The system of claim 1 wherein the controller is further configured to cause the plurality of light emitting elements to emit the light for a predetermined amount of time in response to the door being closed.

8. The system of claim 1 wherein the enclosure further includes a connector configured to attach the enclosure to a railing system in a patient room, and a power source coupled to the plurality of light emitting elements and configured to transfer energy to the plurality of light emitting elements to power the plurality of light emitting elements.

9. The system of claim 1 wherein the enclosure further includes a status indicator configured to output data corresponding to a status of the plurality of light emitting elements of the enclosure.

10. The system of claim 1 wherein
the frame, the door, and the back cover each have an oval shape.

11. The system of claim 1 wherein the enclosure further includes a first reflective surface configured to be located between the door and the cavity and a second reflective surface configured to be located between the back cover and the cavity, the first reflective surface and the second reflective surface each being configured to reflect the light generated by at least a portion of the plurality of light emitting elements into the cavity.

12. The system of claim 1 further comprising a first hook configured to be coupled to the frame and to support a headset of the stethoscope, and a second hook configured to receive a diaphragm of the stethoscope.

13. A system for sterilizing and wireless tethering of a stethoscope, the system comprising:
a portable electronic device configured to be coupled to a stethoscope and having a wireless transmitter configured to transmit a signal; and
an enclosure defining a cavity for housing the stethoscope and having:
a sensor configured to detect a door close event in response to a door being closed,
a plurality of light emitting elements configured to emit light at a wavelength designed to damage or destroy microbes,
a wireless receiver configured to receive the signal transmitted by the wireless transmitter of the portable electronic device,
a controller coupled to the wireless receiver and configured to:
determine a notification event in response to the portable electronic device being further from the enclosure than a predetermined distance based on the signal received by the wireless receiver,
determine the door close event based on data detected by the sensor, and
control the plurality of light emitting elements to emit the light in response to determining the door close event,
a frame at least partially defining the cavity,
the door configured to open to allow access to the cavity and to close to enclose the stethoscope within the cavity,
a back cover,
a front board having a first plurality of light emitting elements of the plurality of light emitting elements and configured to be coupled to the door,
a back board having a second plurality of light emitting elements of the plurality of light emitting elements and configured to be coupled to the back cover, and
a circuit board configured to support the controller.

14. The system of claim 13 wherein the controller is further configured to cause a notification to be transmitted to a remote device in response to determining the notification event.

15. The system of claim 13 wherein
the frame, the door, and the back cover each have an oval shape.

16. A method for sterilizing and wireless tethering of a stethoscope, the method comprising:

transmitting, by a wireless transmitter of a portable electronic device configured to be attached to a stethoscope, a signal;

receiving, by a wireless receiver of an enclosure, the signal;

determining, by a controller of the enclosure, a notification event in response to the portable electronic device being farther from the enclosure than a predetermined distance based on the signal received by the wireless receiver;

detecting, by a sensor, a door of the enclosure being closed; and controlling, by the controller, a plurality of light emitting elements of the enclosure to emit light at a wavelength designed to damage or destroy microbes in response to the door of the enclosure being close;

wherein the enclosure includes:
a frame at least partially defining a cavity for receiving the stethoscope,
the door configured to open to allow access to the cavity and to close to enclose the stethoscope within the cavity,
a back cover,
a front board having a first plurality of light emitting elements of the plurality of light emitting elements and configured to be coupled to the door,
a back board having a second plurality of light emitting elements of the plurality of light emitting elements and configured to be coupled to the back cover, and
a circuit board configured to support the controller.

17. The method of claim 16 further comprising at least one of:

controlling, by the controller, at least one of a speaker or visible light source to emit an audible or visible notification in response to determining the notification event; or causing, by the controller, a notification to be transmitted to a remote device in response to determining the notification event.

18. The method of claim 16 further comprising causing, by the controller, sterilization record data to be transmitted to a central hub, the sterilization record data corresponding to at least one of a time or a frequency at which the plurality of light emitting elements emitted the light.

19. The method of claim 18 further comprising at least one of:

storing, by the central hub, the sterilization record data; or encrypting and transmitting, by the central hub, the sterilization record data to a cloud server for storage.

* * * * *